United States Patent [19]

Abe et al.

[11] Patent Number: 4,486,406

[45] Date of Patent: Dec. 4, 1984

[54] HAIR RINSE COMPOSITION

[75] Inventors: Yoshiaki Abe, Tokyo; Hiroshi Watanabe, Funabashi, both of Japan

[73] Assignee: Kao Soap Co, Ltd., Tokyo, Japan

[21] Appl. No.: 339,630

[22] Filed: Jan. 15, 1982

[30] Foreign Application Priority Data

Feb. 20, 1981 [JP] Japan ................................. 56-5923
Oct. 2, 1981 [JP] Japan ............................. 56-157111

[51] Int. Cl.$^3$ .......................... A61K 7/06; A61K 7/08
[52] U.S. Cl. .................................... 424/70; 424/342; 424/361; 424/362; 424/365
[58] Field of Search ..................... 424/70, 365, 342

[56] References Cited

U.S. PATENT DOCUMENTS 2,197,467  4/1940  Evans et al. ................... 568/644 X

FOREIGN PATENT DOCUMENTS

| 3809M | 1/1966 | France | 424/342 |
| 49-19046 | 2/1974 | Japan | 424/70 |
| 197607 | 7/1976 | Japan | 424/342 |
| 0079313 | 6/1980 | Japan | 424/70 |
| 0124711 | 9/1980 | Japan | 424/70 |
| 0118411 | 9/1980 | Japan | 424/70 |

OTHER PUBLICATIONS

Ash, A Formulary of Cosmetic Preparations, 1977, pp. 124 to 127.

*Primary Examiner*—Dale R. Ore
*Attorney, Agent, or Firm*—Oblon, Fisher, Spivak, McClelland & Maier

[57] ABSTRACT

A hair rinse composition comprising α-mono(methyl-branched alkyl) glyceryl ethers of the formula

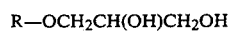

$$R-OCH_2CH(OH)CH_2OH$$

wherein R represents a methyl-branced saturated hydrocarbon having 12–24 carbon atoms, with or without use of quaternary ammonium salts in combination. The ether is dissolved in an aqueous medium including water, or a combination of water with an organic solvent compatible with water.

2 Claims, No Drawings

HAIR RINSE COMPOSITION

BACKGROUND OF THE INVENTION

1. Field of the Invention

This invention relates to hair cosmetics and more particularly, to a hair rinse composition which comprises α-mono(methyl-branched alkyl) glyceryl ethers as its effective component and can impart softness and antistatic property to hair after washing.

2. Description of the Prior Art

In order to eliminate many evils involved on washing of hair, hair rinses comprised of quaternary ammonium salts such as distearyldimethylammonium chloride as effective component are conventionally used at the time of rinsing of hair.

Hair rinses are used to impart softness, smoothness, anti-static property and the like to hair but incorporation of quaternary ammonium salts alone does not procude a satisfactory effect as regards softness and smoothness. Accordingly, in order to overcome this drawback, it is the general practice to incorporate oils such as higher alcohols, glycerides, liquid paraffin and the like.

That is, it has been considered most preferable to use emulsified dispersion systems of suitable oils and quaternary ammonium salts in combination. However, quaternary ammonium salts have no capability of stably emulsifying and dispersing oils in amounts sufficient for showing their effect and there have been made attempts to incorporate nonionic surface active agents exhibiting a higher degree of hydrophilic property so as to keep the emulsion and dispersion system stable. However, highly hydrophilic nonionic surface active agents have a function of considerably lowering the rinsing effect. Accordingly, a hair rinse which comprises nonionic surface active agents in combination with quaternary ammonium salts and oils cannot show a satisfactory rinsing effect.

Generally speaking, hair rinse compositions which have been known to us do not necessarily show a satisfactory rinsing effect, i.e. they cannot impart adequate softness, smoothness, antistatic property to hair. Thus, there is a demand of developing a hair composition of more excellent quality.

SUMMARY OF THE INVENTION

It is accordingly an object of the present invention to provide a hair rinse composition which comprises as its effective component α-mono(methyl-branched alkyl) glyceryl ethers whereby hair can be imparted with agreeable softness and desirable antistatic property.

It is another object of the invention to provide a hair rinse composition which exhibits good hair rinsing effects when applied not only to hair after washing in a manner similar to known compositions, but also to hair before washing.

The above objects can be achieved, according to the invention, by a hair rinse composition which comprises 0.1–30% by weight of an α-mono(methyl-branched alkyl) glyceryl ether of the formula (I)

$$R-OCH_2CH(OH)CH_2OH \quad (I)$$

in which R represents a methyl-branched saturated hydrocarbon having 12–24 carbon atoms, the ether having been dissolved in an aqueous medium.

In a preferred aspect, the composition further comprises a quaternary ammonium salt.

DETAILED DESCRIPTION AND EMBODIMENTS OF THE INVENTION

This compound of the formula (I) is a novel compound and can be prepared, for example, by reacting an alkyl halide of the formula R—X (in which X represents a halogen atom and R has the same meaning as defined above) with an alkali metal alcoholate of isopropylidene glycerol by a usual manner to give 2,3-o-isopropylidene-1-o-methyl-branched alkyl glyceryl ether and then hydrolyzing it.

Among α-mono(methyl-branched alkyl) glyceryl ethers, preferable ethers are those of the formula (I) in which R represents a group of the formula (II)

$$CH_3-(CH_2)_m-\underset{\underset{CH_3}{|}}{CH}-(CH_2)_n- \quad (II)$$

in which m is an integer of 2 to 14, and n is an integer of 3 to 11 provided that the sum of m and n is an integer of 9 to 21. More preferably, in the formula (II), the sum of m and n is an integer of 11 to 17 (i.e. the total number of carbon atoms in the alkyl group is 14 to 20) and most preferably the sum of m and n is 15. Moreover, it is preferable that the branched methyl group is joined to near the center of the alkyl main chain.

The physical properties of a typical α-mono(methyl-branched alkyl) glyceryl ether are shown below.

| methyl-branched alkyl group | melting point | specific density (30° C.) | viscosity (30° C.) |
|---|---|---|---|
| methyl-branched stearyl (mainly composed of groups of the formula (II) in which m = 7, n = 8) | 23° C. | 0.912 | 856 cp |

The hair rinse composition according to the present invention can be prepared by dissolving 0.1–30 wt%, preferably 0.1–15 wt%, of α-mono(methyl-branched alkyl) glyceryl ethers in water and if necessary, in a suitable solvent such as alcohol, propylene glycol, glycerine or the like. Preferably, in order that the 5% solution have such a pH of 3–8 as of ordinary hair rinses, organic acids such as citric acid, lactic acid and the like, inorganic acids such as phophoric acid, hydrochloric acid and the like, inorganic alkalis such as caustic soda, and organic alkalis such as triethanolamine are added for adjustment of the pH.

The hair rinse composition of the invention may further comprise quaternary ammonium salts which are an ordinarily employed component of hair rinse, by which a more excellent hair rinse effect can be obtained. The quaternary ammonium salts useful in the invention are compounds represented by the general formula (III)

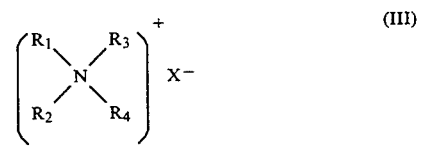

in which one or two or $R_1$, $R_2$, $R_3$ and $R_4$ are independently a long-chain alkyl group or long-chain hydroxyalkyl group having 8–20 carbon atoms, the others represent an alkyl group having 1–3 carbon atoms, a hydroxyalkyl group having 1–3 carbon atoms, a benzyl group or a polyoxyethylene group in which the total of addition moles is below 10, and X represents a halogen atom or an alkylsulfate group having 1–2 carbon atoms. Preferable example of quaternary ammonium salt include distearyldimethylammonium chloride, stearyldimethylammonium metasulfate, N-stearyl-N, N, N-tri(-polyoxyethylene) ammonium chloride (3 moles added in total), cetyltriethyl-ammonium bromide, stearyldimethylammonium chloride and the like.

When an α-mono(methyl-branched alkyl) glyceryl ether and a quaternary ammonium salt are used in combination to prepare a hair rinse, it is preferable to use 0.1–20%, preferably 0.5–5%, of the ether and 0.1–20%, preferably 0.5–5%, of the quaternary ammonium salt. Less amounts than 0.1% of the ether are unfavorable since a satisfactory effect cannot be obtained, whereas larger amounts than 20% are disadvantageous in that it is difficult to keep the rinse composition stable.

If necessary, other additives such as fatty higher alcohols, lanolin oils, esters, liquid paraffin, higher fatty acids and the like oils, bactericides, perfumes and the like may be added to the hair rinse composition of the invention.

The present invention is particularly described by way of examples and references, which should not be construed to limit the invention.

Reference 1

Into a 20 l autoclave were charged 4,770 g of isopropyl isostearate (Emery 2310 isopropyl isostearate, commercially available form United States Emery Co., Ltd.) and 239 g of a copper-chromium catalyst (Nikki K.K.). Then, hydrogen gas was charged under a pressure of 150 kg/cm$^2$ and the reaction mixture was heated up to 275° C. After hydrogenation at 275° C. under 150 kg/cm$^2$, the reaction product was cooled, after which the residue of catalyst was removed by filtration to obtain 3,500 g of a crude product. The crude product was distilled under reduced pressure to obtain 3,300 g of colorless transparent isostearyl alcohol as a distillate of 80°–167° C./0.6 mmHg. The isostearyl alcohol (methyl-branched stearyl alcohol) had an acid value of 0.05, a saponification value of 5.5, and a hydroxyl value of 181.4, and showed absorption peaks at 3,340 and 1,055 cm$^{-1}$ in IR (liquid film) and at δ3.50 (broad triplet, —CH$_2$—OH) in NMR (CCl$_4$ solvent). The gas chromatograph revealed that the alcohol was a mixture composed of about 75% of an alcohol having an alkyl group whose carbon atoms are 18 in number (in formula (II), the sum of m and n is 10) and the balance of alcohols having alkyl groups having 14 and 16 carbon atoms, respectively, the methyl-branched groups being positioned in the vicinity of the central portion of the alkyl main chain.

Reference 2

(i) A 5 l reaction container equipped with a thermometer, a reflux condenser, a dropping funnel, a nitrogen gas-introducing tube and an agitator was provided, into which 2,444 g of the isostearyl alcohol obtained in Reference 1 was charged. Thionyl chloride was dropped from the dropping funnel in the steam of nitrogen gas while agitating. The reaction mixture generated heat, accompanied by simultaneous generation of a gas. The temperature of the reaction mixture was raised up to 31° C. at the initial stage of the reaction but gradually lowered as an amount of thionyl chloride increased down to about 18° C. At the time, the reaction mixture was heated to about 40° C., followed by continuing the dropping of thionyl chloride. After the generation of the gas had become gentle, the reaction mixture was heated to 70°–80° C., whereupon the gas again generated violently, followed by dropping thionyl chloride. At the time when no generation of the gas was recognized, the dropping of thionyl chloride was stopped. The total amount of dropped thionyl chloride was 2,200 g. The reaction product was cooled and was continueously agitated at 70°–80° C. for about 1 hour.

The reaction product was cooled and distilled to remove a low boiling fraction (mainly composed of unreacted thionyl chloride) at 40°–50° C. The resulting residue was cooled in ice, to which pieces of ice were added portion by portion while agitating. It was confirmed that violent generation of the gas was stopped, after which ether was added and then water was added, followed by agitating sufficiently. The ether phase was collected and neutralized with sodium bicarbonate. After distillation of the solvent, the residue was distilled under reduced pressure to obtain 2,217 g of isostearyl chloride from a distillate of 103°–163° C./0.1–1 mmHg.

IR (liquid film): 725, 650 cm$^{-1}$.

NMR (CCl$_4$): δ3.50 (triplet—C$\underline{H}_2$Cl).

(ii) A 5 l reaction container equipped with a thermometer, an agitator, a dropping funnel and a Dean-Stark trap was provided, into which were charged 798 g of isopropylidene glycerol, 1,500 ml of xylene, 340 g of 93% sodium hydroxide solution, and 300 g of water, followed by heating under reflux at 130°–140° C. while agitating. From a distillated water/xylene mixture was separated water in the Dean-Stark trap and the separated water was removed to outside of the reaction system and xylene was returned to the reaction system. After heating under reflux for about 16 hours, no distillation of water was recognized, whereupon 777 g of isostearyl chloride prepared in (i) was dropped in about 30 minutes. After completion of the dropping, the reaction mixture was heated under reflux for further 9 hours at 130°–140° C. to complete the reaction. After cooling, the sodium chloride settled in the reaction container was removed by filtration and the solvent was distilled off under reduced pressure. Then, 800 g of a distillate of 176°–206° C./0.25–0.50 mmHg was obtained. The distillate was found to be 2,3-o-isopropylidene-1-o-isostearyl glyceryl ether.

IR (liquid film) : cm$^{-1}$, 1,200–1,260, 1,050–1,120 (c-o stretching vibration).

NMR(CCl$_4$): δ 3.1–4.2 (multiplet,

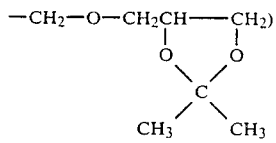

(iii) A 5 l reaction container equipped with an agitator, a thermometer, and a reflux condenser was provided, into which was charged 1,103 g of the isopropylideneisostearyl glyceryl ether obtained in (ii), followed by adding 1,500 ml of ethanol and 2,000 ml of 0.1N sulfuric acid. The mixture was heated under reflux at 80°–85° C. with agitation. After about 10 hours, the reaction was followed by the gas chromatograph, revealing that the hydrolysis of the isopropylideneisostearyl glyceryl ether was completely carried out. After cooling, the reaction system was allowed to stand thereby separating into an oil phase and an aqueous phase. The aqueous phase was extracted with ether and the extract was combined with the oil phase, followed by adding an aqueous solution of sodium bicarbonate to neutralize the remaining acid. After collection of the organic phase, the solvent was removed by distillation under reduced pressure, followed by drying under conditions of 100° C./0.1 mmHg for 3 hours, thereby obtaining 900 g of a colorless transparent liquid of α-mono(isostearyl) glyceryl ether.

IR (liquid film): 3,400, 1,050–1,140 cm$^{-1}$.
NMR(CCl$_4$): δ, 3.2–3.8 (multiplet,

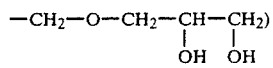

Acid value: 0.08, Saponification value: 0.36, Hydroxyl value: 313.8, Iodine value: 0.32.

EXAMPLE 1

Hair Rinse Composition:
Rinse ingredient (Table 1): 2.5 (wt%)
Water: 97.5
The both components were uniformly mixed.
Rinse Treatment:
Hair which had been washed by a usual manner was immersed in an aqueous 5% solution of each hair rinse composition, for 5 minutes, rinsed with running water for 1 minute, dried with towel, and then dried under air-conditioned conditions (20° C., 65% RH) for 24 hours to give a sample to be tested.
Evaluation:
(1) Hair Softness
Each treated hair (40–50μ) was subjected to a bending moment measuring instrument (KES-FZ, made by K. K. Kato Tekko-sho) to measure its bending moment, which was given by an average of ten measured values.
(2) Sensory Evaluation
Each treated hair was evaluated by an expert panel of ten members and the evaluation was given by an average value of the members.

| Evaluation Standard | |
|---|---|
| +2 | Very good |
| +1 | Slightly good |
| 0 | Moderate |
| −1 | Slightly poor |

Results:
As shown in Table 1.

TABLE 1

| Rinse Component | Hair Softness (g. cm) | Sensor Evaluation |
|---|---|---|
| Products of Invention | | |
| α-mono(methyl-branched alkyl) glyceryl ether obtained in | 0.2 | +1.7 |

TABLE 1-continued

| Rinse Component | Hair Softness (g. cm) | Sensor Evaluation |
|---|---|---|
| Reference 1 | | |
| α-mono(methyl-branched alkyl) glyceryl ether obtained in Reference 2 | 0.2 | +1.5 |
| Comparative products | | |
| α-monoleyl glyceryl ether (celakyl alcohol) | 0.8 | +0.2 |
| distearyldimethylammonium chloride | 0.2 | +1.0 |
| oleic acid monoglyceride | 0.4 | +0.2 |
| stearic acid monoglyceride | 1.0 | −0.1 |
| sorbitan monooleate | 0.8 | −0.3 |
| Control | | |
| water | 0.9 | −0.7 |

EXAMPLE 2

2% (by weight) of the α-mono(methyl-branched alkyl) glyceryl ether obtained in Reference 1, 1.5% of cetyl alcohol and 96.5% of water were mixed and heated at 70° C. and then cooled to room temperature, followed by adding suitable amounts of a perfume and a dyestuff to obtain a hair rinse.

This rinse was used to treat hair before washing and then washed. The hair after washing revealed an excellent rinsing effect of the hair rinse.

EXAMPLE 3

A number of hair rinse compositions of the following formulations were prepared and the formulating effect was determined by measuring a combing force of hair under wet and dry conditions. The results are shown in Table 2.

Formulation:

| Cationic surface active agent | 2.0 (%) |
|---|---|
| α-mono(methyl-branched alkyl) glyceryl ether (in the general formula (III) m = 7, n = 8), or comparative compounds (Table 2) | 2.0 |
| Water | 96.0 |

Measurement of Combing Force:
20% of Japanese female hairs (15 cm long) which had never been subjected to beauty treatments such as cold perm, bleaching and the like were bundled. This hair bundle was immersed in 500 ml of water of 40° C. dissolving 10 g of a hair rinse for 30 seconds, rinsed with running water for 30 seconds, and towel-dried. The semidried hair bundle after drying with towel (wet state: about 0.7 g of water/g of hair) and a dried hair bundle which had been dried for 5 minutes by means of a dryer (dry state: about 0.1 g of water/g of hair) were subjected to a strain gauge to measure a combing strength (20° C.). The measurement was repeated twenty times and an average of the measured values was defined as the combing strength.
Results:
As will be apparent from the results of Table 2, the hair rinses of the invention exhibited excellent combing strengths under dry and wet states.

TABLE 2

| | Cationic Surface Active Agent | α-Mono(methyl-branched alkyl) glyceryl ether or Comparative Compound | Combing Force- dry | wet |
|---|---|---|---|---|
| Products of | cetyltrimethylammonium | α-mono(issostearyl) glyceryl | 107 | 111 |

TABLE 2-continued

| | Cationic Surface Active Agent | α-Mono(methyl-branched alkyl) glyceryl ether or Comparative Compound | Combing Force- dry | wet |
|---|---|---|---|---|
| Invention | chloride distearyltrimethylammonium chloride | ether α-mono(isostearyl) glyceryl ether | 98 | 76 |
| Comparative Products | cetyltrimethylammonium chloride | — | 275 | 206 |
| | | α-monooleyl glyceryl ether | 185 | 156 |
| | | stearic acid mono glyceride | 299 | 283 |
| | distearyldimethylammonium chloride | — | 196 | 171 |
| | | α-monooleyl glyceryl ether | 217 | 179 |
| | | stearic acid monoglyceride | 198 | 175 |
| | heptylbenzyldimethylammonium chloride | — | 371 | 316 |
| | | α-mono(isostearyl) glyceryl ether | 249 | 317 |
| | | α-monooleyl glyceryl ether | 256 | 291 |
| | | stearic acid monoglyceride | 297 | 288 |
| | — | α-mono(isostearyl) glyceryl ether | 251 | 365 |
| | — | α- monoleyl glyceryl ether | 271 | 323 |
| | — | stearic acid monoglyceride | 311 | 305 |

EXAMPLE 4

Several α-mono(methyl-branched alkyl) glyceryl ethers having different values of m and n in the formula (III) were used to prepare rinse compositions of the following formulation. The combing force was measured in the same manner as in Example 1 using the thus prepared compositions. The results are as shown in Table 3.

Formulation:

| Cetyltrimethylammonium chloride | 2.0 (%) |
|---|---|
| α-mono(methyl-branched alkyl) glyceryl ether | 2.0 |
| Water | 96.0 |

Results:

TABLE 3

| | | In Formula (III) | | Combing Force (g) | |
|---|---|---|---|---|---|
| Composition | (No.) | m | n | dry | wet |
| Comparative product | 1 | 1 | 6 | 175 | 201 |
| Products of Invention | 2 | 7 | 6 | 105 | 115 |
| | 3 | 9 | 6 | 104 | 110 |
| | 4 | 11 | 6 | 121 | 129 |

EXAMPLE 5

Creamy Hair Rinse:

| A. Distearyltrimethylammonium chloride | 1.0 (%) |
|---|---|
| B. Stearyltrimethylammonium chloride | 1.0 |
| C. α-mono(isostearyl) glyceryl ether (m = 7, n = 8) | 2.0 |
| D. Hydroxyethyl cellulose | 0.7 |
| E. Glycerine | 5.0 |
| F. Citric acid | 0.2 |
| G. Dye | suitable amount |
| H. Perfume | suitable amount |
| I. Water | balance |

I was heated to 70° C., to which were added D, G and F while agitating to dissolve them in I, followed by adding a mixture of A, B, C and E heated to 70° C. The mixture was cooled while agitating, to which was added H at 45° C., followed by cooling to 30° C. to obtain the present composition.

This composition showed excellent properties and storage stability.

EXAMPLE 6

Transparent Hair Rinse:

| A. Cetyltrimethylammonium chloride | 1.0 (%) |
|---|---|
| B. α-mono(isostearyl) glyceryl ether (m = 7, n = 8) | 2.5 |
| C. Ethanol | 10.0 |
| D. Hydroxypropylmethyl cellulose | 0.5 |
| E. Polyoxyethylene hardened castor oil (80 E.O.) | 0.5 |
| F. Perfume | Suitable amount |
| G. Dye | Suitable amount |
| H. Water | balance |

G was dissolved in H, to which was added a liquid mixture of A, B, C, D, E, F to obtain the present composition.

This composition showed excellent properties and storage stability.

What is claimed is:

1. A method of rinsing hair comprising applying to hair a composition of pH of 3-8 capable of imparting softness and antistatic property comprising 0.1-30% by weight of an α-mono (methyl-branched alkyl) glyceryl ether of the general formula (I)

$$ROCH_2CH(OH)CH_2OH \quad (I)$$

in which R represents a group of the following formula (II)

$$CH_3-(CH_2)_m-\underset{\underset{CH_3}{|}}{CH}-(CH_2)_n- \quad (II)$$

in which m is an integer of 2-14, and n is an integer of 3-11, provided that m+n is an integer of 9-21, the glyceryl ether having been dissolved in an aqueous medium.

2. A method of rinsing hair comprising applying to hair a composition of pH of 3-8 capable of imparting softness and antistatic property comprising the following ingredients (A) and (B): (A) 0.1-20 wt % of at least one quaternary ammonium salt of the general formula (III)

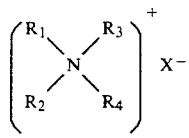

in which one or two of $R_1$, $R_2$, $R_3$ and $R_4$ represent a long-chain alkyl group or a long-chain hydroxyalkyl group having 8-20 carbon atoms, the others represent an alkyl group having 1-3 carbon atoms, a hydroxyalkyl group having 1-3 carbon atoms, a benzyl group or a polyoxyethylene group in which the total of addition moles is below 10, and X represents a halogen atom or an alkylsulfate having 1-2 carbon atoms; and (B) 0.1-20 wt % of an α-mono(methyl-branched alkyl) glyceryl ether of the general formula (I)

$$R-OCH_2CH(OH)CH_2OH \qquad (I)$$

in which R represents a group of the following formula (II)

$$CH_3-(CH_2)_m-\underset{\underset{CH_3}{|}}{CH}-(CH_2)_n- \qquad (II)$$

in which m is an integer of 2-14, and n is an integer of 3-11, provided that m+n is an integer of 9-21.

* * * * *

UNITED STATES PATENT AND TRADEMARK OFFICE
CERTIFICATE OF CORRECTION

PATENT NO. : 4,486,406

DATED : December 4, 1984

INVENTOR(S) : Abe et al.

It is certified that error appears in the above-identified patent and that said Letters Patent is hereby corrected as shown below:

On the title page

- - [30] Foreign Application Priority Data

January 20, 1981  Japan    56-5923

October 2, 1981   Japan    56-157111  - -

Signed and Sealed this

Eighteenth Day of June 1985

[SEAL]

Attest:

DONALD J. QUIGG

Attesting Officer   Acting Commissioner of Patents and Trademarks